US00PP25500P3

(12) United States Plant Patent
Budagovsky

(10) Patent No.: US PP25,500 P3
(45) Date of Patent: May 5, 2015

(54) APPLE TREE ROOTSTOCK NAMED 'B 70-20-20'

(50) Latin Name: *Malus domestica*
Varietal Denomination: B 70-20-20

(71) Applicant: Michurinsk State Agrarian University, Tambov Region, Michurinsk (RU)

(72) Inventor: Valentin Ivanovich Budagovsky, Michurinsk (RU)

( * ) Notice: Subject to any disclaimer, the term of this patent is extended or adjusted under 35 U.S.C. 154(b) by 0 days.

(21) Appl. No.: 13/694,505

(22) Filed: Dec. 6, 2012

(65) Prior Publication Data
US 2014/0165240 P1 Jun. 12, 2014

(51) Int. Cl.
*A01H 5/00* (2006.01)

(52) U.S. Cl.
USPC ..... Plt./174

(58) Field of Classification Search
USPC ..... Plt./174
See application file for complete search history.

*Primary Examiner* — Annette Para
(74) *Attorney, Agent, or Firm* — The Webb Law Firm

(57) ABSTRACT

A new and distinct *Malus domestica* plant used as a rootstock that exhibits a good rooting ability and vegetative propagation.

4 Drawing Sheets

Botanical classification: *Malus domestica.*
Varietal denomination: 'B 70-20-20'.

BACKGROUND OF THE INVENTION

The present invention comprises a new and distinct cultivar of clonal *Malus domestica* used as a rootstock known by the varietal name 'B 70-20-20'. The new variety was discovered in the Tambov region of Russia in 1970. The new variety is the result of a cross between apple rootstock 57-469 (B9×13-14), (female parent, unpatented) and apple rootstock 57-344 (Naliv Aliy×B9), (male parent, unpatented). The purpose of the breeding program was to develop dwarf apple tree rootstocks. The new variety exhibits similar anthocyanic color of the leaves, bark, and wood to both parents, but exhibits fewer root suckers and has better rooting ability, vegetative propagation, and vigor than both parents. When compared to EMLA 111 rootstock (unpatented), 'B-70-20-20' has a stronger and more extensive root system, improved cold tolerance, and exhibits better layer bed production characteristics. Further, the new variety is similar in anthocyanin color to unpatented B 118 (54-118), but is more vigorous. The new variety has been trial and field tested and has been found to retain its distinctive characteristics and remain true to type through successive propagations. The following characteristics distinguish 'B 70-20-20' from other varieties known to a representative of the breeder:

1. The anthocyanin color of the leaves, bark, and wood;
2. Good rooting ability and vegetative propagation;
3. The growth of a root shoot in the mother bed is strong; and
4. The root shoots are thick and straight, but prone to overgrowth.

DESCRIPTION OF THE DRAWINGS

The accompanying photographic drawings illustrate one year old 'B 70-20-20' rootstocks produced from layer bed propagation and grown in Dundee, Oreg. The color of the leaves is a little darker than normal for the rootstocks in fall because the weather had not turned cold in the growing location. However, the color is as nearly true as is possible with color illustrations of this type.

DESCRIPTION OF THE PLANT

Figure 1:
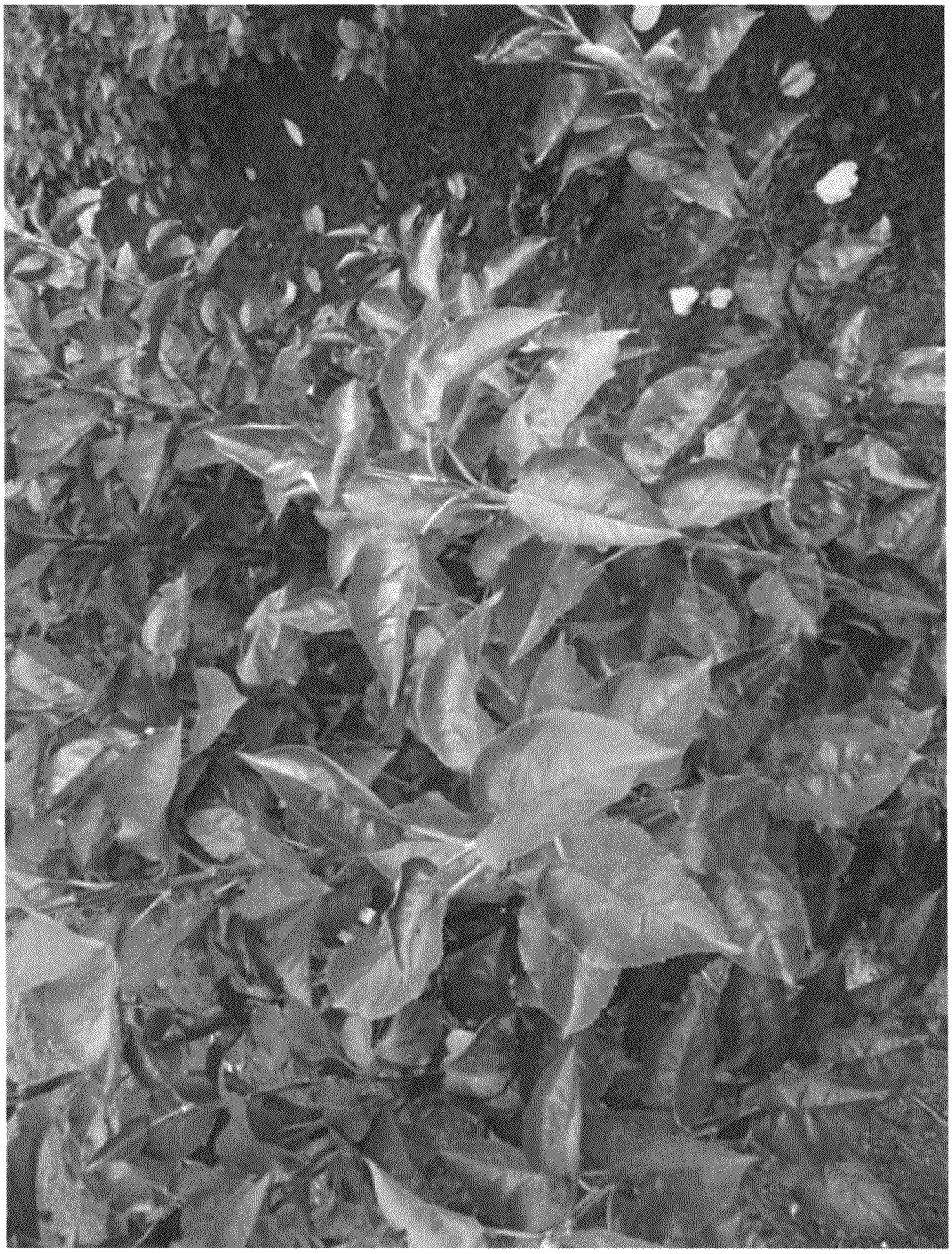
FIG. 1 shows 'B 70-20-20' rootstocks in layer beds.
Figure 2:
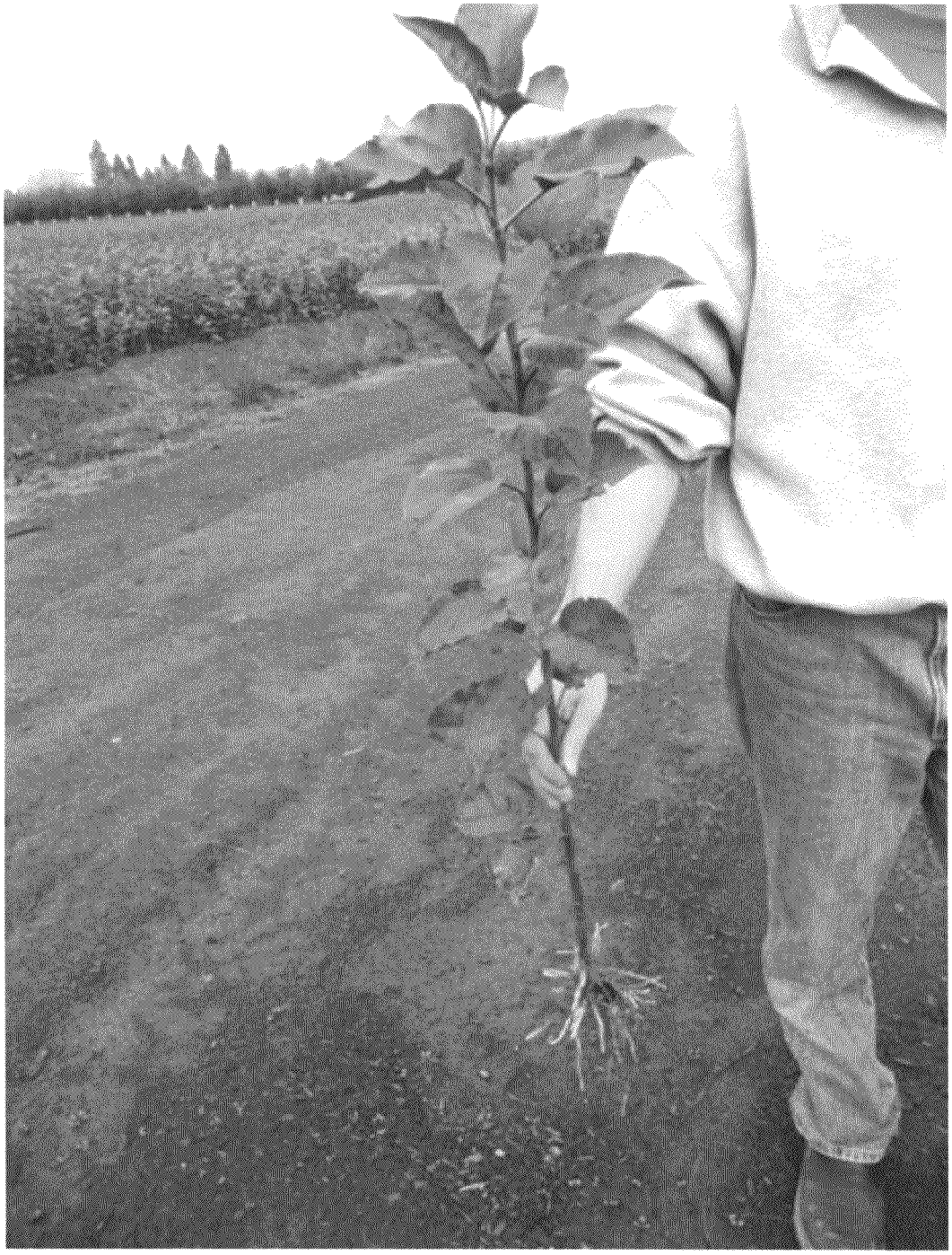
FIG. 2 is a view of an unrooted 'B 70-20-20' rootstock.
Figure 3:
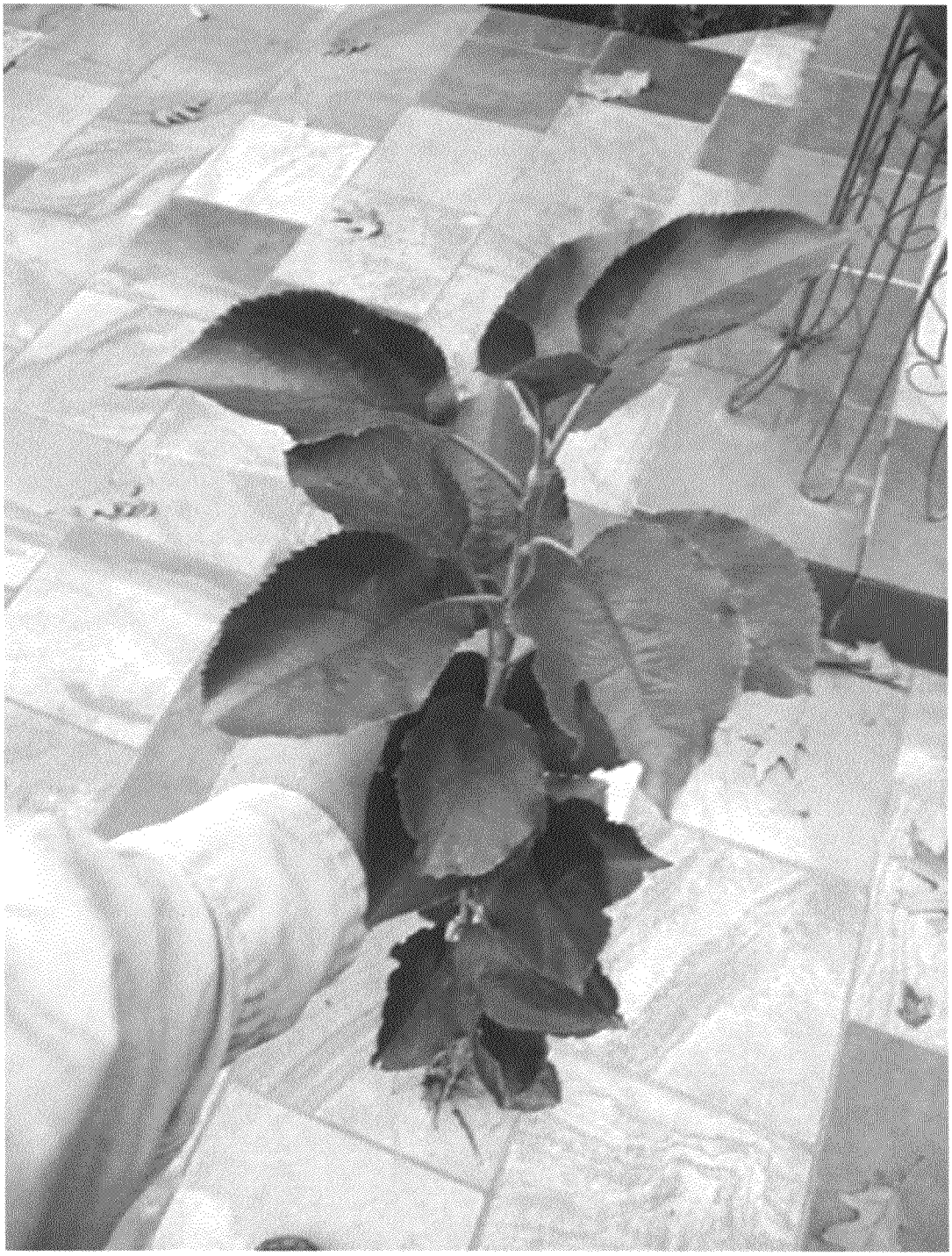
FIG. 3 is a close-up view of the leaves of the new variety.
Figure 4:
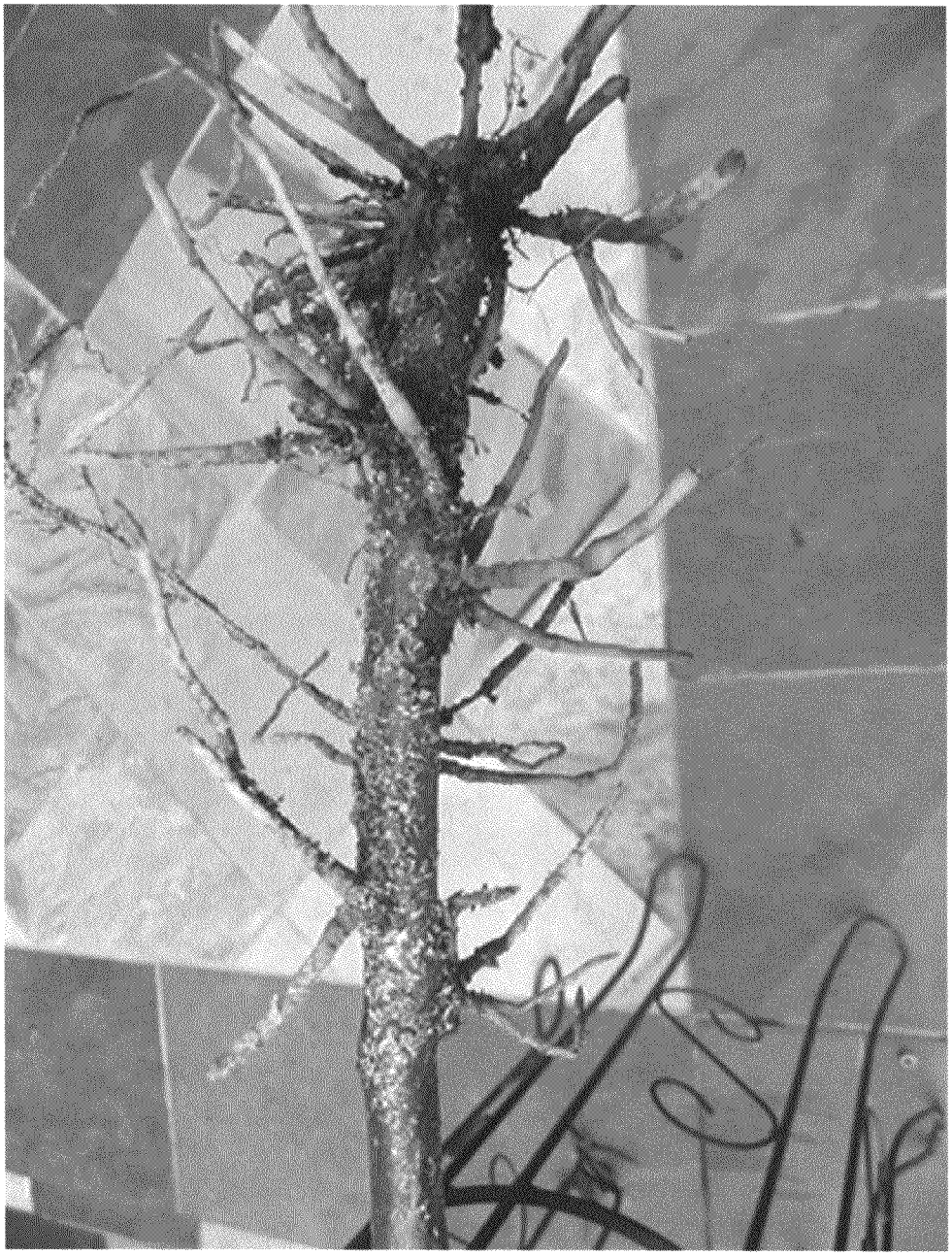
FIG. 4 is a close-up view of the root system of 'B 70-20-20'

The following detailed description sets forth the characteristics of the new cultivar. Some of the data that defines these characteristics was collected on 10-year-old rootstocks produced by asexual reproductions and propagation carried out in the Tambov region of Russia. However, some of the data was collected outside under natural daylight on one-year-old plants produced by asexual reproductions and propagation carried out in Dundee, Oreg.; this data is indicated by an asterisk. When available, color references follow The R.H.S. Colour Chart of The Royal Horticultural Society of London.

TREE

Size: 3.7 m.; *5/8 inches in diameter and 34 inches tall.
Vigor: Vigorous; *Strong—equal to MM 106 and B 118 apple rootstocks.
Rooting: Strong.
Density: *Heavy.
Form: Reverse egg-shaped.
Production: High.
Growth type: *Straight and vertical in layer beds without side shoots.
Fruit timing: Six years after planting in the Tambov region of Russia.
One year shoot color: *59A.
One year cambium color: *134C.
Pubescence: *Present on top 30 cm. of a one year shoot that is absent later on in growth.

Trunk:

*Bark color*.—Dark cherry.

*Lenticels*.—Length: *1.0 mm. Width: *1.0 mm. Color: *163D. Shape: *Round to oval. Density: *Medium to light. Bud arrangement: *Alternate and about 30 cm apart.

Leaves:

*Length*.—*80 mm.

*Width*.—*68 mm.

*Form*.—Egg-shaped.

*Texture*.—*Smooth on top and bottom surfaces.

*Thickness*.—*Moderate.

*Apex*.—*Acute.

*Base*.—*Mostly symmetrical.

*Margin*.—*Serrate, saw-formed crenation.

*Pubescence*.—Upper surface: *None on young and old leaves — some present on petioles and veins. Lower surface: Very slight to none.

*Color*.—Young leaves: Upper surface: *131A. Lower surface: *137C. Mature leaves: Upper surface: *135A. Lower surface: *138B.

*Petiole*.—Length: *31 cm. Diameter: *3 mm. Color: *59B. Shape: *Straight and not tapered.

*Veins*.—Venation description: *Raised and in a v-shaped pattern that meets at the center of the leaves. Color (both surfaces): *The upper main vein at the center of a leaf is 59B, away from the center the vein color is 63A.

Bloom timing: From May 10th to May 22th; average is May 14th. As the variety is used as a rootstock, plants are not typically grown to flowering stage and, as such, flower data is not available.

Fruit:

*Date of picking*.—August 15th.

*Size*.—Axial diameter: 6.5 cm. Transverse diameter: 5.0 cm.

*Skin*.—Tendency to crack: No. Color: Raspberry pink.

*Eating quality*.—Mediocre.

*Use*.—As a rootstock; interstem.

Tree winter hardiness: Roots can tolerate temperatures down to −16° C.; upper areas of rootstocks can tolerate temperatures down to −40° C.

Drought tolerance: Average.

MULTIPLICATION ABILITY

Layering: Up to nine root shoots from one plant at the 3$^{rd}$ year. Rooting ability is 4.3 on a 5-grade scale.

Hardwood cuttings: Rooting output is 60-70%.

Softwood cuttings: Rooting output is 90-95%.

PATHOGEN RESISTANCE

Fungal disease: Relatively resistant; can be affected by powdery mildew some years.

Insects: Average resistance to aphids.

PERFORMANCE AS ROOTSTOCK UPON GRAFTING

Root sprouts (suckering): No suckering.

Anchorage: Very good.

Compatibility: Good with tested varieties.

Vigor: 0-15% more vigorous than trees on 54-118.

I claim:

1. A new and distinct variety of *Malus domestica* rootstock, as illustrated and described herein.

* * * * *